(12) United States Patent
Snyder

(10) Patent No.: US 10,426,299 B2
(45) Date of Patent: Oct. 1, 2019

(54) EXFOLIATION AND BODY CREAM APPLICATION MITT

(71) Applicant: James Snyder, Hollywood, CA (US)

(72) Inventor: James Snyder, Hollywood, CA (US)

( * ) Notice: Subject to any disclaimer, the term of this patent is extended or adjusted under 35 U.S.C. 154(b) by 27 days.

(21) Appl. No.: 15/963,908

(22) Filed: Apr. 26, 2018

(65) Prior Publication Data

US 2019/0125138 A1    May 2, 2019

Related U.S. Application Data

(60) Provisional application No. 62/486,805, filed on Apr. 18, 2017.

(51) Int. Cl.
| | | |
|---|---|---|
| A45D 34/04 | (2006.01) | |
| A47K 7/03 | (2006.01) | |
| A47K 7/04 | (2006.01) | |
| A61H 7/00 | (2006.01) | |
| A61M 35/00 | (2006.01) | |
| A47K 7/02 | (2006.01) | |

(52) U.S. Cl.
CPC ............... *A47K 7/03* (2013.01); *A45D 34/04* (2013.01); *A47K 7/02* (2013.01); *A61H 7/003* (2013.01); *A45D 2200/1054* (2013.01); *A61H 2201/165* (2013.01); *A61H 2201/1692* (2013.01); *A61M 35/003* (2013.01)

(58) Field of Classification Search
CPC ............ A45D 34/04; A45D 2200/1009; A45D 2200/1018; A45D 2200/1036; A45D 2200/1054; A61M 35/003; A61M 35/006; A61M 35/10; A61H 7/003; A61H 2201/165; A61H 2201/1692; A47K 7/02; A46B 5/04; A47L 13/18; A47L 13/19; A47L 13/16
See application file for complete search history.

(56) References Cited

U.S. PATENT DOCUMENTS

| | | | |
|---|---|---|---|
| 6,250,829 B1* | 6/2001 | Brower | A45D 34/04 15/227 |
| 2006/0078516 A1 | 4/2006 | Parker et al. | |
| 2007/0118963 A1 | 5/2007 | Snyder | |
| 2007/0223988 A1 | 9/2007 | Gruenbacher et al. | |
| 2010/0130988 A1 | 5/2010 | Bolton | |
| 2010/0287720 A1* | 11/2010 | Kayata, Sr. | A47K 7/03 15/227 |

FOREIGN PATENT DOCUMENTS

EP    1153553 A1    11/2001

* cited by examiner

*Primary Examiner* — David J Walczak
(74) *Attorney, Agent, or Firm* — Law Office of Michael O'Brien

(57) ABSTRACT

An exfoliation and body cream application mitt is configured to apply a thickened liquid to a human user. The exfoliation and body cream application mitt has a back side and a front side joined to one another forming a pocket therebetween. The front side is adapted to accomplish exfoliation and the back side is adapted to accomplish lotion application. A soft fabric arranged within the back side and configured to gently spread body creams, foams and lotions to a skin surface. A wrist section is arranged between the back side and the front side, defining an opening for receiving a hand of a user.

18 Claims, 4 Drawing Sheets

EXFOLIATION AND BODY CREAM APPLICATION MITT

RELATED APPLICATION

This application claims priority to provisional patent application U.S. Ser. No. 62/486,805 filed on Apr. 18, 2017 the entire contents of which is herein incorporated by reference.

BACKGROUND

The embodiments herein relate generally to beauty products for exfoliation, and gloves and mitts for applying lotion to the skin.

Prior to embodiments of the disclosed invention exfoliation and body cream application was inefficient. Embodiments of the disclosed invention solve this problem.

Various exfoliating bath towels, exfoliating gloves, exfoliating sponges, and lotion application mitts are known in the art. Each of these items serves a different purpose for essentially the same purpose, which is to aid in cleansing the body.

The exfoliating bath towel is a loose piece of cloth that the user can use with exfoliating lotions and soaps to cleanse the body. A disadvantage of the bath towel is that it can slip out of the hand easily and it cannot maintain continuous exfoliating grit without repeatedly adding more exfoliating lotion.

The exfoliating bath glove is similar to a bath towel except that it provides full severable functionality of all of the fingers. With this format the fingers are able to grip solid exfoliating soap. This format also allows a user to fully exfoliate body contours. However, a disadvantage of the bath glove is that it does not provide continuous suds without the repeated handling of usage of exfoliating lotion.

The bath sponge is made out of elastic netting that is formed into a multi-layered, ruffled ball with a string attached. The ruffled layers of the ball allow for the capture of more soap bubbles and allows for continuous suds with less applications of exfoliating location or soap. A disadvantage of the bath sponge is that it cannot be maneuvered as well in delicate curvatures of the body.

The lotion application mitt is a mitt that a user uses to apply lotion onto the body. The lotion can be tanning lotion. With this format the mitt is able to prevent the lotion from getting onto the hands, thereby reducing the need to wash one's hands. A disadvantage of the lotion application mitt is that it applies lotion to the outer layer of a user's skin which is dead and falls off, and thus leaves a spotted, streaked, or uneven tan.

In view of the above mentioned disadvantages existing in the conventional exfoliating bath towel, exfoliating glove, exfoliating sponge, and lotion application mitt, the present invention provides an improved exfoliation mitt. The present invention provides for dry exfoliation giving a user the freedom and convenience of water-free exfoliation and lotion application. The present invention overcomes the disadvantages of the aforementioned, conventional products, and provides a product that can thoroughly exfoliate the user's skin with less amounts of exfoliating lotion and can apply lotion more evenly to the freshly exposed skin of the disclosed invention to solve this problem.

SUMMARY

An exfoliation and body cream application mitt is configured to apply a thickened liquid to a human user. The exfoliation and body cream application mitt has a back side and a front side joined to one another forming a pocket therebetween. The front side is adapted to accomplish exfoliation and the back side is adapted to accomplish lotion application. A soft fabric arranged within the back side and configured to gently spread body creams, foams and lotions to a skin surface. A wrist section is arranged between the back side and the front side, defining an opening for receiving a hand of a user.

In some embodiments, a hydrophilic layer of material can be attached to the back side. The hydrophilic layer of material can be a polymer film such as a polyurethane film. A soft foam layer can be joined to the polymer film.

In some embodiments, a gentle exfoliation fabric can be located in a palm area of the front side. A deep exfoliation fabric can be located in a fingertip area of the front side. The gentle exfoliation fabric can be omnidirectional such that exfoliation is equal in every direction the exfoliation and body cream application mitt is moved. The deep exfoliation fabric can further comprise a transverse grain such that exfoliation is optimized when the exfoliation and body cream application mitt is moved in a lateral direction. The gentle exfoliation fabric is made from one member of a gentle exfoliation fabric set consisting of: bamboo, sisal, sauna cloth, viscose, coarse polyurethane foam and treated polyurethane foam. The soft fabric can be one member of a soft fabric set consisting of: a brushed fabric, a suede fabric, a woven fabric, a woven loop fabric, a nonwoven fabric, a knitted fabric, a knitted loop fabric, a spun bond fabric, an airlaid fabric, a terrycloth, a velvet, and a hydro-entangled nonwoven fabric. A soft foam can be arranged beneath the soft fabric.

A gripping layer can be attached to the layer of the soft foam and selected from one member of a gripping layer set consisting of: a grip material applied in a printed pattern, a grip material applied in a continuous layer, and a tacky layer.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
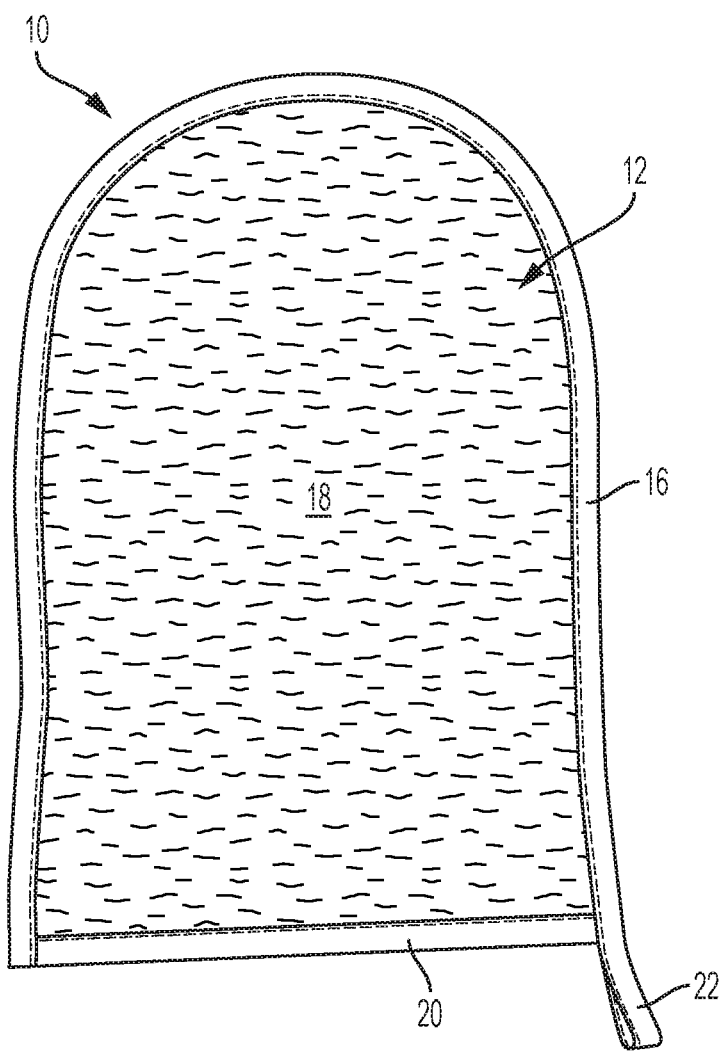
FIG. 1 shows a front view of one embodiment of the present invention.
Figure 2:
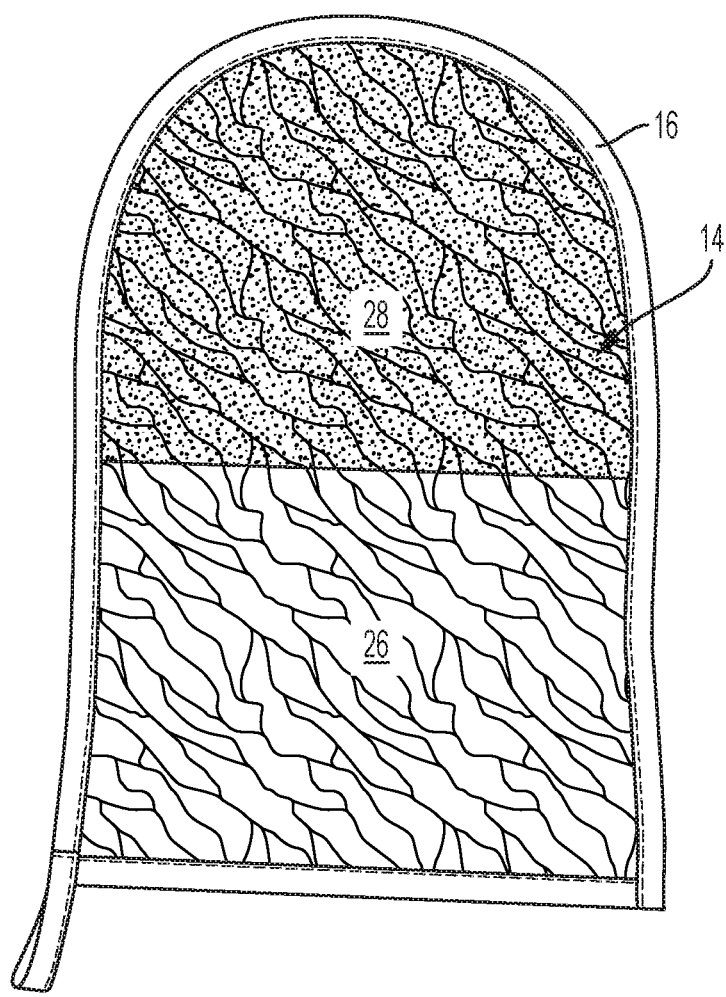
FIG. 2 shows a back view of one embodiment of the present invention.
Figure 3:
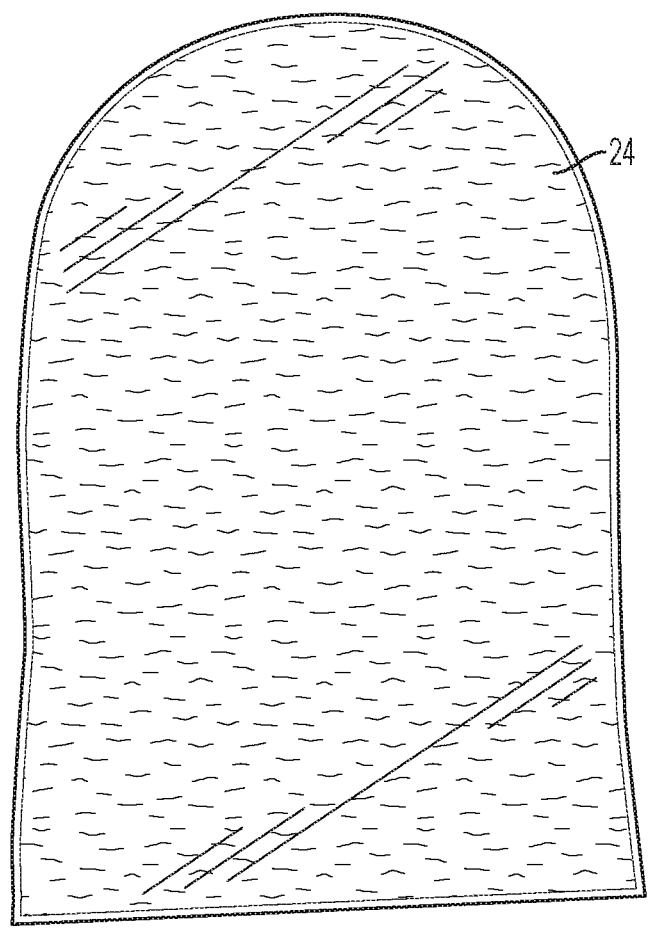
FIG. 3 shows a front detail view of one embodiment of the present invention.
Figure 4:
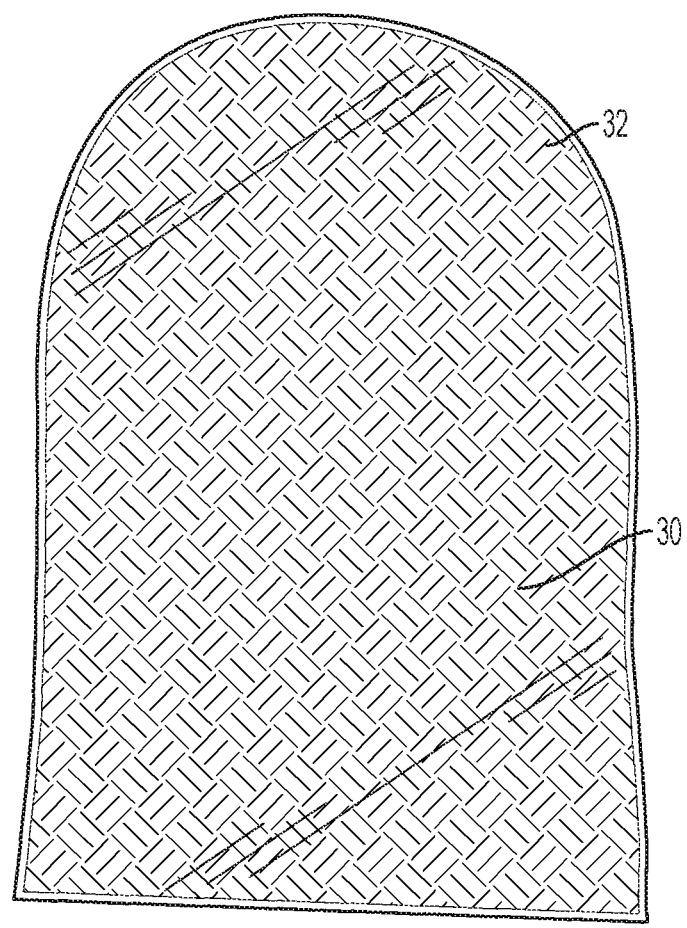
FIG. 4 shows a back detail view of one embodiment of the present invention.

An exfoliation and body cream application mitt 10 is configured to apply a thickened liquid to a human user. The exfoliation and body cream application mitt 10 has a back side 12 and a front side 14 joined to one another with a seam 16 to form a pocket therebetween. The front side is 14 adapted to accomplish exfoliation and the back side 12 is adapted to accomplish lotion application. A soft fabric 18 arranged within the back side and configured to gently spread body creams, foams and lotions to a skin surface. A wrist section 20 is arranged between the back side and the front side, defining an opening for receiving a hand of a user. A loop 22 can be attached to the seam 16 or wrist section 20.

In some embodiments, a hydrophilic layer of material 24 can be attached to the back side 12. The hydrophilic layer of material 24 can be a polymer film such as a polyurethane film. The polymer film is most effective when the polymer film possesses a moisture vapor transmission rate of over 100 grams per square meter per 24 hours. The polymer film can be between 0.0005 inches and 0.005 inches in thickness. A soft foam layer can be joined to the polymer film. In some embodiment of the invention, the polymer film is made up of a film layer that is ideally between 0.0002" and 0.020" thick and more ideally between 0.0005" and 0.010" thick and even more ideally between 0.0005" and 0.005" thick. The polymer film layer as a film can be made up of any polymeric material that will resist the cosmetic, but ideal materials include polyethylene and polypropylene films or polyurethane or hytrel films. There can be advantages to using an elastic film such as polyurethane as the fit to the hand can be better and the entire glove can be made to be elastic or stretch to fit. The use of a film such as hytrel or polyurethane can also be beneficial due to its ability to transmit moisture or sweat through the film without allowing the cosmetic to come through. This is not as necessary when the polymer film layer is only on one side of the mitt under the application side, as the sweat can move out on the other side, but in certain embodiments of the invention it may be beneficial to cover all sides of the mitt with a polymer film or hydrophobic layer, and in such cases a moisture-breathable film layer may be more important than the single sided polymer film. A barrier layer can be other than a film as well and can be a hydrophobic treatment or treated material instead.

The barrier layer on the application side may be placed between the other fabric/foam layers in the lamination process, or it may be on the back surface of the inside of the mitt. In the event the barrier is interior to the soft foam layer, it can be important in preferred embodiments of the invention that the inside surface have enough frictional coefficient such that the hand does not slip around during the application of the cosmetic but is able to grip the inside surface. Thus, disposing the barrier layer between the outside surface and the soft foam layer (if used) can be an effective way to accomplish this.

In some embodiments, a gentle exfoliation fabric 26 can be located in a palm area of the front side 14. A deep exfoliation fabric 28 can be located in a fingertip area of the front side 14. The gentle exfoliation fabric 26 can be omnidirectional such that exfoliation is equal in every direction the exfoliation and body cream application mitt 10 is moved. The deep exfoliation fabric 28 can further comprise a transverse grain such that exfoliation is optimized when the exfoliation and body cream application mitt 10 is moved in a lateral direction. The gentle exfoliation fabric 26 can be made from one member of a gentle exfoliation fabric set consisting of: bamboo, sisal, sauna cloth, viscose, coarse polyurethane foam and treated polyurethane foam. The deep exfoliation fabric 28 can be one member of a soft fabric set consisting of: a brushed fabric, a suede fabric, a woven fabric, a woven loop fabric, a nonwoven fabric, a knitted fabric, a knitted loop fabric, a spun bond fabric, an airlaid fabric, a terrycloth, a velvet, and a hydro-entangled nonwoven fabric. The two levels of exfoliating layers are disposed on the opposite side of the glove from the application side. It has been found to be ideal in some preferred embodiments of the invention that the coarser or more abrasive exfoliation material be placed at the top of the mitt where the fingers are located. This allows for greater pressure to be applied to areas of the body requiring the greater exfoliation. Ideal materials for exfoliation include Bamboo, Sisal, Sauna Cloth or Viscose or a coarse polymeric material such as polyurethane that can also be surface treated to be more abrasive or it can be any other material with exfoliating properties.

It is generally ideal that the exfoliating material chosen be omnidirectional, so that the exfoliation and body cream application mitt 10 can be used in any direction. The omnidirectional even exfoliation surface is much more critical for the exfoliation and body cream application mitt 10, as if a user is exfoliating with a separate device, they can rotate it in the hand, whereas the Exfoliation and body cream application mitt 10 is locked in one orientation, thus it is ideal in preferred embodiments that one or both of the exfoliating materials be omnidirectional and without a specific orientation.

In the event that one or both of the exfoliating material chosen has an orientation, then it is preferable that the orientation be such that the exfoliation takes place when moving the hand to the side, and not toward the fingertips.

In still another embodiment of the invention, one or both of the exfoliating materials can be removed and reoriented using Velcro or any other temporary or semi-temporary attachment method. This allows the user to either select different degrees or levels of exfoliation or allows the user to re-orient the direction of the exfoliation if it is not an omnidirectional material.

In some embodiments of the invention it has been found to be ideal that the [Exfoliation] exfoliation and body cream application mitt 10 be made of sufficiently elastomeric materials such that the [Exfoliation] exfoliation and body cream application mitt 10 can grip or fit more snugly on the hand and to thus be more accurate in application and exfoliation In still other embodiments of the invention, it has been found that it is ideal to have the exfoliating material inset on the exfoliating side of the glove, sufficient that the user does not accidentally contact the exfoliating material while using the application side. An inset distance allows for some protection against accidentally contacting the rough exfoliating material during application of the cosmetic.

Other materials that would be suitable for the application side of the exfoliation and body cream application mitt 10 would include any woven or knitted or nonwoven material with a soft and evenly textured surface. Such suitable other materials would include also unbroken loop fabrics such as terry cloths or loop fabrics, or broken loop fabrics such as velvets and the like. In addition, nonwoven materials of various types can make ideal surface fabrics and have the advantage that they can be less expensive and yet highly regular. Examples of such nonwovens that are ideal for the present invention are hydro-entangled or spun bonded or spun bonded polyesters, nylons, polypropylenes, cottons or any other soft polymer or organic material in nonwoven form. A hydro-entangled polyester material laminated to a polyurethane foam is also ideal for an inexpensive embodiment of the invention.

In addition, the surface material may be made up of a fine cell polyurethane foam by itself, so long as the surface of the foam is soft and fine and regular enough to apply the cosmetic in a non-streaky manner. When a nonwoven polyurethane foam is used as the surface of the present invention, there is generally not a need to apply the additional soft layer of polyurethane material to the back. This additional soft polyurethane layer may still make sense when the surface polyurethane layer is significantly more expensive due to its fine surface. In addition, the added layer of foam would allow the application of the hydrophobic or barrier layer in the application side, whilst still leaving the inside layer of foam for a good gripping surface for the fingers and hand inside the exfoliation and body cream application mitt 10.

A soft foam 30 can be arranged beneath the deep exfoliation fabric 28. The soft foam can be a micro-cellular polyurethane foam that is at least 0.040 inches thick but no more than 0.250 inches thick. In one embodiment of the present invention, the ideal thickness range for the soft foam layer behind the brushed fabric has been found to be between 1/32 inch to 1/2 inch thickness and more specifically, a range of 1/16 inch to 1/4 inch thick. More specifically a thickness of 3/32 inch to 3/16 inch has been found to be ideal for this application. The soft foam layer can is ideally bonded to the back of the soft fabric layer using a lamination process. Flame lamination can be ideal for this bonding, wherein the polyurethane foam is briefly exposed to a gas flame and becomes tacky, so that it can be applied to the soft fabric.

A gripping layer 32 can be attached to the layer of the soft foam 30 and selected from one member of a gripping layer set consisting of: a grip material applied in a printed pattern, a grip material applied in a continuous layer, and a tacky layer. To enhance the inside grip, a grip material can be deposited in either a continuous layer or in a printed pattern such as dots to enhance the grip inside the mitt.

A hydrophilic material can be treated into an outer surface of the soft fabric in order for the thickened liquid to wick away from the soft fabric and spread evenly. In some embodiments, at least one active agent can be embedded in at least one member of the side set consisting of the front side and the back side. The at least one active agent can be at least one member of an active agent set consisting of: an antimicrobial agent, an antifungal agent, a silver agent, a copper agent, and a nanoparticle agent. It is also advantageous in certain embodiments of the present invention to use active agents such as silver, copper or other materials that have antimicrobial or antifungal properties, or a blend of these materials. Silver or copper can be ideal for this, especially when in nanoparticle size, as they are non-pesticide methods of killing bacteria or fungus that might otherwise grow on the damp mitt. These materials can be applied or be part of the fibers themselves, preventing them from being loose. Nanoparticle seized active agents are particularly useful if being used within the fiber due to their small size. Other active agents such as vitamin C or other skin aiding or medicinal actives may be used in the present invention.

In addition, it is envisioned in still another embodiment of the invention, that a reservoir and dispensing mechanism may be attached to the application side of the mitt, such that the cream or gel or cosmetic can be moved directly from the attached reservoir onto or into the application surface. The reservoir device can be designed to apply a single material or to simultaneously blend multiple materials in ratio, thus allowing for materials that might be unstable if already mixed to be easily blended as they are pumped or moved from the reservoir device.

The exfoliation and body cream application mitt 10 is made by a series of unique steps. First making a selection from gentle exfoliating fabrics such as cotton, nylon, flax linen, soft natural loofah, microfiber, terry cloth, or an equivalent. Then making a selection from deep exfoliating fabrics such as coarse sisal fibers, hemp fibers, jute, bamboo fibers, or nylon fibers fortified with pumice powder, or an equivalent. Coupling both types of exfoliating cloths on the same plane by sewing. Lining the exfoliation part with a waterproof lining such as nylon. Making a soft foam side that is also lined with a waterproof lining such as nylon. Finally sandwiching both sides and affixing them by a coupling means such as sewing or hot compression so that the inside is waterproof and the outside has an exfoliation side and a soft foam side. As an additional element, adding a fabric hook, or a piece of string to allow for the mitt to be hung on a shower hook.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶ 6. In particular, any use of "step of" in the claims is not intended to invoke the provision of 35 U.S.C. § 112, ¶ 6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. An exfoliation and body cream application mitt, configured to apply a thickened liquid to a human user; the exfoliation and body cream application mitt comprising:
   a back side and a front side joined to one another forming a pocket therebetween;
   wherein the front side is adapted to accomplish exfoliation and the back side is adapted to accomplish lotion application;
   a soft fabric arranged within the back side and configured to gently spread body creams, foams and lotions to a skin surface;
   a gentle exfoliation fabric located in a palm area of the front side; and
   a deep exfoliation fabric located in a fingertip area of the front side a wrist section, arranged between the back side and the front side, defining an opening for receiving a hand of a user.

2. The exfoliation and body cream application mitt of claim 1, further comprising: a hydrophilic layer of material, attached to the back side.

3. The exfoliation and body cream application mitt of claim 2, wherein the hydrophilic layer of material is a polymer film.

4. The exfoliation and body cream application mitt of claim 3, wherein the polymer film has a moisture vapor transmission rate of over 100 grams per square meter per 24 hours.

5. The exfoliation and body cream application mitt of claim 3, wherein the polymer film is a polyurethane film.

6. The exfoliation and body cream application mitt of claim 3, wherein the polymer film is between 0.0005 inches and 0.005 inches in thickness.

7. The exfoliation and body cream application mitt of claim 3, further comprising a soft foam layer joined to the polymer film.

8. The exfoliation and body cream application mitt of claim 1, wherein the gentle exfoliation fabric is omnidirectional such that exfoliation is equal in every direction the exfoliation and body cream application mitt is moved.

9. The exfoliation and body cream application mitt of claim 8, wherein the deep exfoliation fabric further comprises a transverse grain such that exfoliation is optimized when the exfoliation and body cream application mitt is moved in a lateral direction.

10. The exfoliation and body cream application mitt of claim 9, wherein the gentle exfoliation fabric is made from one member of a gentle exfoliation fabric set consisting of: bamboo, sisal, sauna cloth, viscose, coarse polyurethane foam and treated polyurethane foam.

11. The exfoliation and body cream application mitt of claim 1, wherein the soft fabric is one member of a soft fabric set consisting of: a brushed fabric, a suede fabric, a woven fabric, a woven loop fabric, a nonwoven fabric, a knitted fabric, a knitted loop fabric, a spun bond fabric, an airlaid fabric, a terrycloth, a velvet, and a hydro-entangled nonwoven fabric.

12. The exfoliation and body cream application mitt of claim 11, further comprising a layer of a soft foam arranged beneath the soft fabric.

13. The exfoliation and body cream application mitt of claim 12, wherein the soft foam is a micro-cellular polyurethane foam.

14. The exfoliation and body cream application mitt of claim 13, wherein the layer of the soft foam is at least 0.040 inches thick but no more than 0.250 inches thick.

15. The exfoliation and body cream application mitt of claim 14, further comprising a gripping layer, attached to a second layer of the soft foam and selected from one member of a gripping layer set consisting of: a grip material applied in a printed pattern, a grip material applied in a continuous layer, and a tacky layer.

16. The exfoliation and body cream application mitt of claim 1, further comprising at least one active agent embedded in at least one member of the side set consisting of the front side and the back side.

17. The exfoliation and body cream application mitt of claim 16, wherein the at least one active agent is at least one member of an active agent set consisting of: an antimicrobial agent, an antifungal agent, a silver agent, a copper agent, and a nanoparticle agent.

18. An exfoliation and body cream application mitt, configured to apply a thickened liquid to a human user; the exfoliation and body cream application mitt comprising:
a back side and a front side joined to one another forming a pocket therebetween;
wherein the front side is adapted to accomplish exfoliation and the back side is adapted to accomplish lotion application;
a soft fabric arranged within the back side and configured to gently spread body creams, foams and lotions to a skin surface; wherein the soft fabric is one member of a soft fabric set consisting of: a brushed fabric, a suede fabric, a woven fabric, a woven loop fabric, a nonwoven fabric, a knitted fabric, a knitted loop fabric, a spun bond fabric, an airlaid fabric, a terrycloth, a velvet, and a hydro-entangled nonwoven fabric;
a hydrophilic material, treated into an outer surface of the soft fabric in order for the thickened liquid to wick away from the soft fabric and spread evenly;
a wrist section, arranged between the back side and the front side, defining an opening for receiving a hand of a user.

* * * * *